US00PP11595P

United States Patent [19]

Westhoff

[11] Patent Number: Plant 11,595

[45] Date of Patent: Oct. 24, 2000

[54] PETUNIA PLANT NAMED 'WESWEI'

[75] Inventor: Heinrich Westhoff, Südlohn-Oeding, Germany

[73] Assignee: Josef + Heinrich Westhoff Gartenbau-Spezialkulturen, Sudlohn-Oeding, Germany

[21] Appl. No.: 09/213,447

[22] Filed: Dec. 17, 1998

[51] Int. Cl.[7] ..... A01H 5/00

[52] U.S. Cl. ..... Plt./356

[58] Field of Search ..... Plt./356

*Primary Examiner*—Howard J. Locker
*Assistant Examiner*—Michelle Kizilkaya
*Attorney, Agent, or Firm*—C. A. Whealy

[57] ABSTRACT

A distinct cultivar of Petunia plant named 'Weswei', characterized by its dark green leaves; numerous pure white flowers; cascading and freely branching growth habit; early flowering; and good weather tolerance, particularly tolerant to rain, wind and low temperatures.

2 Drawing Sheets

BACKGROUND OF THE INVENTION

The present invention relates to a new and distinct cultivar of Petunia plant, botanically known as *Petunia axillaris*, and hereinafter referred to by the cultivar name Weswei.

The new Petunia is a product of a planned breeding program conducted by the Inventor in Südlohn-Oeding, Germany. The new Petunia originated from a cross made by the Inventor in 1996 of the nonpatented *Petunia axillaris* cultivar Sylvana White as the female, or seed, parent with a seedling selection of *Petunia axillaris* identified as Sylvana 95/076 as the male, or pollen, parent.

Asexual reproduction of the new cultivar by terminal cuttings taken at Südlohn-Oeding, Germany, has shown that the unique features of this new Petunia are stable and reproduced true to type in successive generations.

SUMMARY OF THE INVENTION

Plants of the cultivar Weswei have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Weswei'. These characteristics in combination distinguish 'Weswei' as a new and distinct cultivar:

1. Dark green leaves.

2. Numerous pure white flowers.

3. Cascading and freely branching growth habit.

4. Relatively early flowering.

5. Good weather tolerance, particularly tolerant to rain, wind and low temperatures.

Plants of the cultivar Weswei can be compared to plants of the female parent, the cultivar Sylvana White. However in side-by-side comparisons conducted in Südlohn-Oeding, Germany, plants of the cultivar Weswei differ from plants of the cultivar Sylvana White in the following characteristics:

1. Leaves of plants of the new Petunia are larger, more rounded, darker green and have longer petioles than leaves of plants of the cultivar Sylvana White.

2. Plants of the new Petunia have larger flowers than plants of the cultivar Sylvana White.

3. Plants of the new Petunia have pure white-colored flowers whereas plants of the cultivar Sylvana White have very light pink-colored flowers.

4. Plants of the new Petunia have longer and darker green peduncles than plants of the cultivar Sylvana White.

5. Plants of the new Petunia have darker green sepals than plants of the cultivar Sylvana White.

Plants of the cultivar Weswei are similar in flower color to plants of the nonpatented Surfinia White. However in side-by-side comparisons conducted in Südlohn-Oeding, Germany, plants of the cultivar Weswei differ from plants of the cultivar Surfinia White in the following characteristics:

1. Plants of the new Petunia are more compact than plants of the cultivar Surfinia White.

2. Leaves of plants of the new Petunia are smaller and darker green than leaves of plants of the cultivar Surfinia White.

3. Plants of the new Petunia are more floriferous than plants of the cultivar Surfinia White.

4. Plants of the new Petunia flower earlier than plants of the cultivar Surfinia White.

5. Flower petals of plants of the new Petunia do not have as prominent veins as flower petals of plants of the cultivar Surfinia White.

6. Flowers of plants of the new Petunia have longer peduncles than flowers of plants of the cultivar Surfinia White.

7. Flowers of plants of the new Petunia have light lilac-colored stamens and pollen whereas flowers of plants of the cultivar Surfinia White have ivory-colored stamens and pollen.

8. Plants of the new Petunia exhibit better weather tolerance, particularly to rain, than plants of the cultivar Surfinia White.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph on the first sheet comprises a side perspective view of a large basket of plants of the new Petunia.

The photograph on the second sheet comprises a close-up view of a typical flower of the new Petunia. Flower and foliage colors in the photographs may appear different than the actual colors due to light reflectance.

DETAILED BOTANICAL DESCRIPTION

In the following description, color references are made to The Royal Horticultural Society Colour Chart except where general terms of ordinary dictionary significance are used. Twelve-week old plants grown in 12.5-cm containers used for the description were grown under greenhouse conditions which closely approximate commercial production conditions in Südlohn-Oeding, Germany, with average day and night temperatures of 23° C. and 26° C., respectively with an average light level ranging from 3,000 to 50,000 lux.

Botanical classification: *Petunia axillaris* cultivar Weswei.

Parentage:

*Female parent.*—*Petunia axillaris* cultivar Sylvana White, not patented.

*Male parent.*—*Petunia axillaris* seedling selection identified as Sylvana 95/076, not patented.

Propagation:

*Type cutting.*—Terminal vegetative cuttings.

*Time to initiate and develop roots.*—About 14 days at 20° C. soil temperature.

*Rooting habit.*—Numerous, fine, fibrous, and well-branched.

Plant description:

*Form.*—Indeterminate, decumbent, cascading, viscid, glandular pubescent. Appropriate for hanging baskets.

*Branching habit.*—Freely basally branching, lateral branches typically form at every node.

*Plant height* (*from soil level to top of plant plane*).—About 20 cm.

*Area of spread.*—About 85 cm, cascading, decumbent.

*Vigor.*—Moderate.

*Lateral branches.*—Quantity: Typically 14. Length: About 43.5 cm. Diameter: About 2 mm. Internode length: About 4.3 cm. Texture: Moderately pubescent. Color: 144A.

*Foliage description.*—Leaves simple, generally symmetrical and long persisting. Leaf arrangement alternate before flowering, opposite after flowering. Leaves somewhat fleshy, glandular. Foliage tolerant to wind and rain damage. Quantity per lateral branch: Typically about 30. Length: About 5.2 cm. Width: About 2.7 cm. Aspect: Typically horizontal. Shape: Obovate to rotund. Apex: Slightly acute to rounded. Base: Attenuate. Margin: Entire. Texture: Slightly pubescent on both surfaces. Color: Young foliage, upper surface: 137A. Young foliage, lower surface: 137C. Mature foliage, upper surface: 147A. Mature foliage, lower surface: 147B. Venation, both surfaces: 144A. Petiole: Length: About 1.2 cm. Diameter: About 2 mm. Color: 144A.

Flower description:

*Flower type and habit.*—Large, single, salverform flowers, facing upwards, axillary. Calyx five-parted, petals united into a flower tube.

*Natural flowering season.*—Long day responsive, continuously flowers from spring through fall.

*Quantity.*—Very freely flowering with numerous flowers per plant.

*Flower buds.*—Length: About 3.9 cm. Diameter: About 6.6 mm. Shape: Oblong. Color: Apex: 144A. Mid-section: 144A. Base: 157A.

*Corolla.*—Diameter: About 5.6 cm. Flower tube length: About 2.6 cm. Flower tube diameter at distal end: About 1.1 cm. Flower tube diameter at proximal end: About 2.8 mm. Petal length from throat: About 2.75 cm. Petal width: About 2.53 cm. Petal quantity: Five, fused. Petal apex: Rounded and slightly cuspidate. Texture: Smooth and satiny. Color: Petal, upper surface, when opening: 155B. Petal, lower surface, when opening: 157B. Petal, upper surface, opened flower: 155D. Petal, lower surface, opened flower: 155D. Flower throat (inside): 155B. Flower throat, vein: 86A. Flower tube (outside): 144B. Flower tube, vein: 83B to 83C. Petal color, fading to: 157C.

*Sepals.*—Quantity: Five. Length: About 1.5 cm. Width: About 3 mm. Shape: Linear. Apex: Obtuse. Margin: Entire. Aspect: Upright. Texture: Pubescent. Color: Upper surface: 147A. Lower surface: 147B.

*Peduncle.*—Strength: Flexible. Angle: About 38° to stem. Length: About 3.5 cm. Width: Narrow, about 1.1 mm. Texture: Pubescent. Color: 143A.

*Reproductive organs.*—Stamens: Stamen number: Five. Anther shape: Four-parted, roughly oval. Anther size: About 3 mm. Anther color: 69D. Pollen amount: Moderate. Pollen color: 91D. Pistils: Pistil length: About 2.1 cm. Stigma shape: Inverted triangle. Stigma color: 89A. Style length: About 1.7 cm. Style color: 145A. Ovary color: 144C.

Weather tolerance: Good tolerance to rain and wind has been observed. The new Petunia can withstand low temperatures to about -3° C.

Disease resistance: Resistance to diseases common to Petunia has not been observed.

Seed production: Seed production has not been observed.

It is claimed:

1. A new and distinct cultivar of Petunia plant named 'Weswei', as illustrated and described.

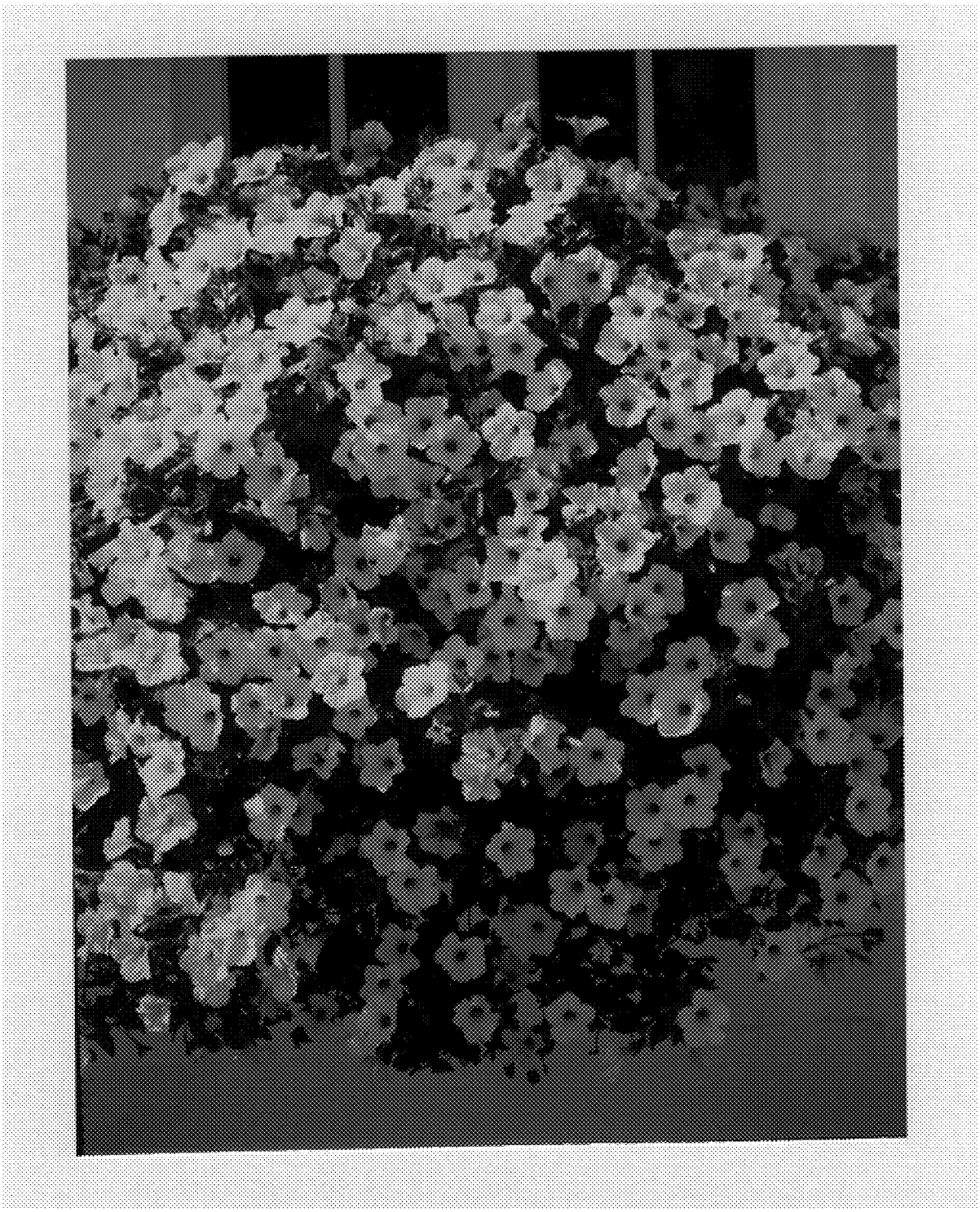

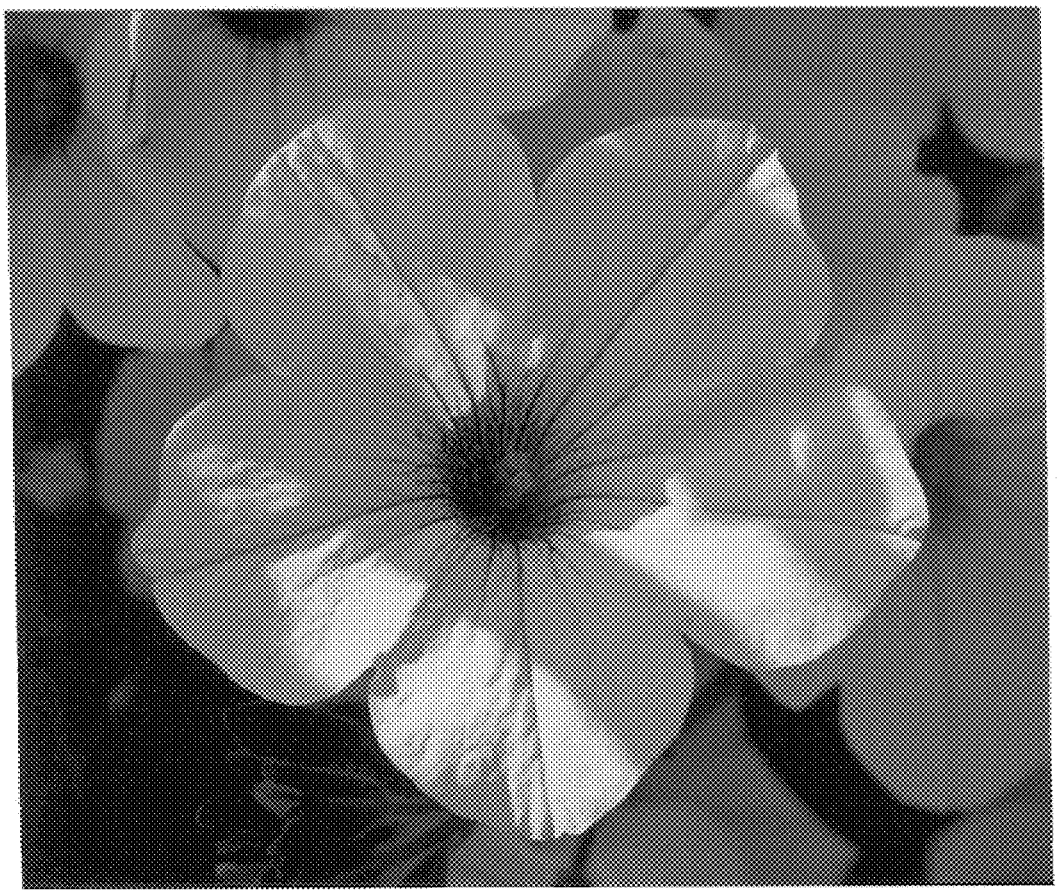

* * * * *